(12) United States Patent
Sugita

(10) Patent No.: US 7,922,717 B2
(45) Date of Patent: Apr. 12, 2011

(54) HIGH-FREQUENCY TREATMENT TOOL FOR ENDOSCOPE

(75) Inventor: Noriyuki Sugita, Saitama (JP)

(73) Assignee: Hoya Corporation, Tokyo (JP)

( * ) Notice: Subject to any disclaimer, the term of this patent is extended or adjusted under 35 U.S.C. 154(b) by 977 days.

(21) Appl. No.: 11/678,169

(22) Filed: Feb. 23, 2007

(65) Prior Publication Data

US 2007/0203487 A1 Aug. 30, 2007

(30) Foreign Application Priority Data

Feb. 28, 2006 (JP) .................. 2006-052689

(51) Int. Cl.
*A61B 18/14* (2006.01)
(52) U.S. Cl. ........................... 606/46; 606/45
(58) Field of Classification Search .............. 606/45–50
See application file for complete search history.

(56) References Cited

U.S. PATENT DOCUMENTS

| 6,217,575 | B1 * | 4/2001 | DeVore et al. ............... 606/41 |
| 6,949,099 | B2 * | 9/2005 | Shiro et al. ................. 606/45 |
| 2005/0215853 | A1 | 9/2005 | Ouchi |
| 2006/0155271 | A1 | 7/2006 | Sugita et al. |
| 2006/0178656 | A1 * | 8/2006 | Sugita et al. ................ 606/1 |
| 2006/0178669 | A1 | 8/2006 | Sugita et al. |
| 2007/0282326 | A1 * | 12/2007 | Sugita ........................ 606/45 |

FOREIGN PATENT DOCUMENTS

| JP | 10-235574 | 9/1998 |
| JP | 2002-113016 | 4/2002 |
| JP | 2004-544 | 1/2004 |
| JP | 2004-231008 | 8/2004 |
| JP | 2005-270240 | 10/2005 |
| JP | 2005-279126 | 10/2005 |

OTHER PUBLICATIONS

English language Abstract of JP 2004-231008, Aug. 19, 2004.
English language Abstract of JP 10-235574, Sep. 8, 1998.
U.S. Appl. No. 11/550,528 to Sugita, which was filed Oct. 18, 2006.
U.S. Appl. No. 11/550,508 to Sugita, which was filed Oct. 18, 2006.
U.S. Appl. No. 11/675,754 to Sugita, which was filed Feb. 16, 2007.
English language abstract of JP 2002-113016.

* cited by examiner

*Primary Examiner* — Michael Peffley
*Assistant Examiner* — Benjamin Lee
(74) *Attorney, Agent, or Firm* — Greenblum & Bernstein P.L.C.

(57) ABSTRACT

A high-frequency treatment tool for an endoscope, having an electrically insulating flexible tube, an operating wire, a high-frequency electrode, which is provided at a distal end of the operating wire and configured to be protrusible and retractable from a distal end of the flexible tube in the axial direction of the flexible tube, and a tubular member, is provided. The tubular member is fitted on the operation wire and immovably attached thereon by plastic deformation, which is caused as at least a part of the tubular member is deformed to interfere with an inner circumferential surface of the flexible tube so that the operating wire is halted with respect to the flexible tube at an arbitrary position in the flexible tube by frictional resistance caused between an interfering part of the tubular member and the inner circumferential surface of the flexible tube.

14 Claims, 6 Drawing Sheets

HIGH-FREQUENCY TREATMENT TOOL FOR ENDOSCOPE

BACKGROUND OF THE INVENTION

The present invention relates to a high-frequency treatment tool, which is inserted through a forceps channel of an endoscope and used for incision of mucous membranes and in vivo tissues inside a human body.

Generally, a high-frequency treatment tool for an endoscope is configured to have an electrically conductive operating wire arranged to be movable in an axial direction thereof in an electrically insulated flexible tube, which is inserted in a forceps channel of the endoscope. Further, a rod-like high-frequency electrode is connected to a tip end of the operating wire so that the high-frequency electrode can be protruded and retracted from a distal end of the flexible tube as the operating wire is advanced and retracted from a proximal end thereof.

In such a configuration, however, due to a security reason, such a high-frequency electrode is configured to be stabilized at a position wherein the operating wire is fully advanced toward the distal end and the electrode is extended to a maximum length thereof so that the length of the high-frequency electrode should not vary during an operation. Accordingly, a length of the high-frequency electrode to be protruded from the tip end of the flexible tube is not adjustable but fixed. Therefore, in some cases, the high-frequency electrode may be too short for an operation to incise in vivo tissue in a certain depth or may be too long for a certain incising operation.

In consideration of the above, a flexible tube provided with a length adaptor at the distal end of the flexible tube has been developed. An example of such an adaptor is disclosed in Japanese Patent Provisional Publication No. 2002-113016 (hereinafter, referred to as '016 publication). The adaptor disclosed in '016 publication is capable of extending and contracting in the axial direction. By coupling the length adaptor of which the length has been adjusted with the distal end of the flexible tube, the length of the high-frequency electrode to be protruded from the length adaptor can be adjusted depending on the incising operation.

With the adaptor, however, the configuration of the endoscope becomes more complicated, and a cost for the endoscope may be increased. Further, when the length of the high-frequency electrode to be protruded is changed, the treatment tool is required to be withdrawn from the forceps channel so that the adaptor can be detached from and reattached to the distal end thereof. Thus, the operation to adjust the length of the high-frequency electrode has been complicated and rather troublesome.

SUMMARY OF THE INVENTION

In view of the foregoing drawbacks, the present invention is advantageous in that there is provided an improved high-frequency treatment tool for an endoscope wherein a length of a high-frequency electrode to be protruded from a distal end of a flexible tube can be arbitrarily adjusted without withdrawing the treatment tool itself from a forceps channel.

According to an aspect of the present invention, a high-frequency treatment tool for an endoscope is provided. The high-frequency treatment tool includes an electrically insulating flexible tube, which is inserted into an instrument channel of the endoscope, an operating wire, which is configured to be electrically conductive and movable inside the flexible tube in an axial direction of the flexible tube, a high-frequency electrode, which is provided at a distal end of the operating wire and configured to be protrusible and retractable from a distal end of the flexible tube in the axial direction of the flexible tube according to movement of the operating wire, and a tubular member fitted on the operation wire and immovably attached thereon by plastic deformation, which is caused as at least a part of the tubular member is deformed to interfere with an inner circumferential surface of the flexible tube so that the operating wire is halted with respect to the flexible tube at an arbitrary position in the flexible tube by frictional resistance caused between an interfering part of the tubular member and the inner circumferential surface of the flexible tube, and the high-frequency electrode to be protruded and retracted from the distal end of the flexible tube is halted in an arbitrary position.

Optionally, a cross-section of the inner circumferential surface of the flexible tube and a cross-section of an outer circumferential surface of the tubular member prior to the plastic deformation may be substantially circular.

Optionally, the tubular member may be plastically deformed inwardly toward an axis of the tubular member in a plurality of axially and circumferentially displaced positions with respect to the axis of the tubular member.

Optionally, the tubular member may be plastically deformed inwardly in two axially and circumferentially displaced positions which are circumferentially separated at an angle of substantially 90 degrees from each other.

Optionally, the tubular member may be plastically deformed inwardly toward the axis of the tubular member in four circumferentially displaced but axially coinciding positions which are circumferentially separated at an angle of substantially 90 degrees from one another.

Optionally, the tubular member may be plastically deformed inwardly toward the axis of the tubular member in a set of four circumferentially displaced but axially coinciding positions which are circumferentially separated at an angle of substantially 90 degrees from each other. The tubular member may be plastically deformed inwardly toward the axis of the tubular member in another set of four circumferentially displaced but axially coinciding positions which are circumferentially separated at an angle of substantially 90 degrees from each other. The two sets of four circumferentially displaced but axially coinciding positions may be axially displaced from each other and circumferentially separated at an angle of 45 degrees from each other.

Optionally, the high-frequency treatment tool may include a stopper at a distal end portion thereof. A length of the high-frequency electrode to be protruded from the distal end of the flexible tube may be restricted when at least one of a distal end of the operating wire and a distal end of the tubular member becomes in contact with a proximal end portion of the stopper.

Optionally, the operating wire may be configured to have a core wire and a plurality of strand wires twisted around the core wire. The plurality of strand wires may be removed from the operating wire at a distal end portion of the operating wire while a remaining portion of the core wire at the distal end of the operating wire defines to be the high-frequency electrode.

Optionally, the tubular member may be immovably attached to the operating wire at the distal end portion of the operating wire in which the strand wires are maintained around the core wire.

Optionally, the tubular member may be immovably attached to the operating wire at a position closer to a proximal end of the operating wire than the distal end portion of the operating wire. The plurality of strand wires twisted around the core wire may be bundled together by one of brazing and soldering at the distal end portion of the operating wire in which the strand wires are maintained around the core wire.

Optionally, the tubular member may be formed to have a protruded portion, which protrudes further from a distal end portion of the operating wire toward the distal end of the flexible tube when the tubular member is immovably attached to the operating wire. The proximal end of the high-frequency electrode may be attached to the distal end of the operating wire inside the protruded portion of the tubular member.

Optionally, the high-frequency electrode and the operating wire may be electrically conducted via the tubular member.

Optionally, the tubular member may be configured to have a smaller outer diameter portion, in which an outer diameter thereof is formed to be smaller than an outer diameter of the remaining portion of the tubular member.

Optionally, the high-frequency electrode may be formed to have a shape of a straight rod.

DETAILED DESCRIPTION OF THE EMBODIMENTS

Hereinafter, referring to the accompanying drawings, according to illustrative embodiments of the invention will be described.

First Embodiment

Figure 1:
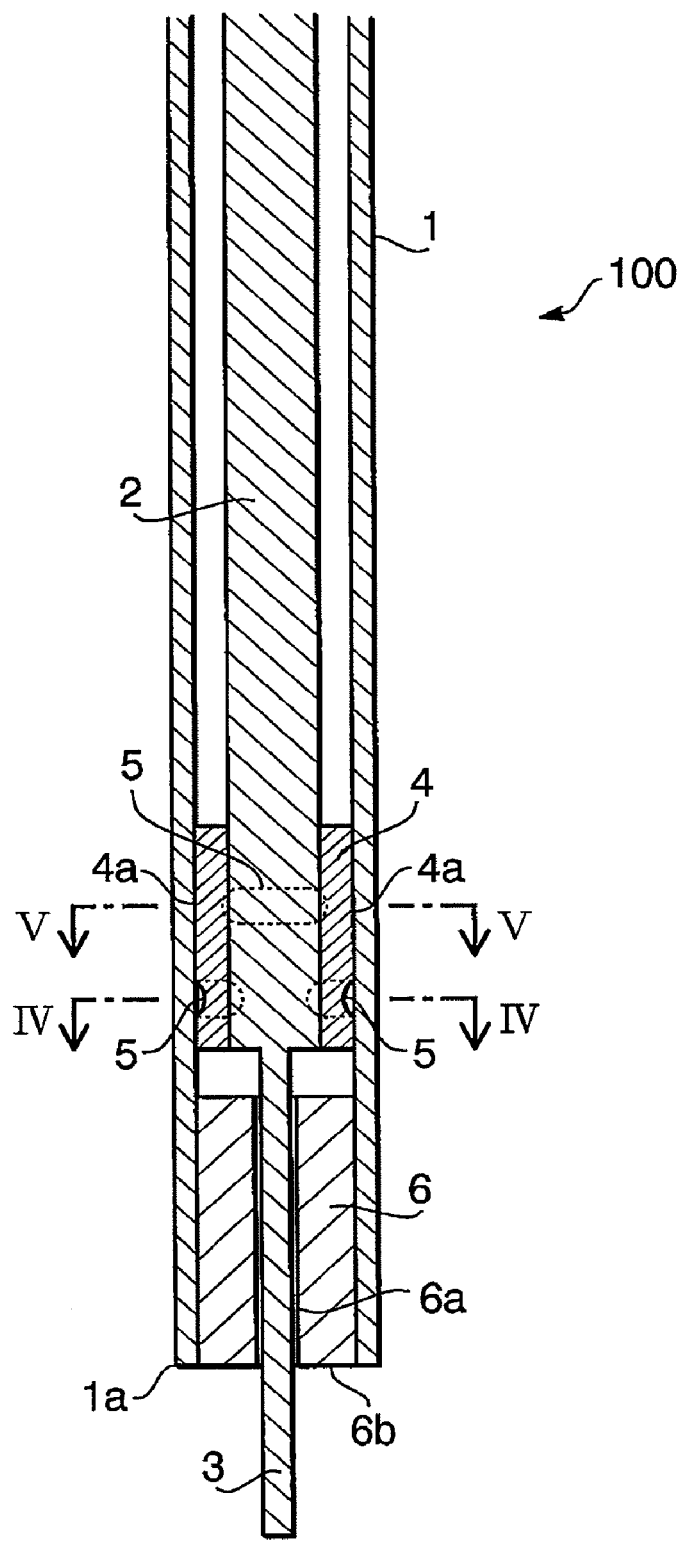
FIG. 1 is a cross-sectional side view of a distal end portion of a high-frequency treatment tool for an endoscope according to a first embodiment of the invention.

FIG. 1 is a cross-sectional side view of a distal end portion of a high-frequency treatment tool 100 for an endoscope according to a first embodiment of the invention. The high-frequency treatment tool 100 includes a flexible tube 1, which is to be inserted into a forceps channel of the endoscope and is made of an electrically insulating material such as polytetrafluoroethylene with a cross-section thereof in general having a shape of an approximate circle.

The high-frequency treatment tool 100 further includes an operating wire 2, which is configured to be movable in an axial direction of the flexible tube 1 and is arranged inside and throughout an entire length of the flexible tube 1 with clearances provided between inner surfaces of the flexible tube 1. In the present embodiment, the operating wire 2 is configured to have a core wire and a plurality of strand wires twisted around the core wire. The operating wire 2 can be advanced and retracted by operating an operation unit (not shown) of the treatment tool 100 which is connected to a proximal end of the flexible tube 1.

Further, the high-frequency treatment tool 100 is provided with a rod-like high-frequency electrode 3 at a distal end portion of the operating wire 2. The high-frequency electrode 3 is configured to be protruded and retracted from a distal end 1a of the flexible tube 1 as the operating wire 2 is advanced/withdrawn.

In the present embodiment, the strand wires are removed from the operating wire 2 at a distal end portion thereof, and solely the core wire is extended to define the high-frequency electrode 3. In this configuration, a process to connect the operating wire 2 with the high-frequency electrode 3 can be omitted.

The distal end portion of the operating wire wherein the core wire remains and the strand wires are removed is covered with a clinching pipe 4. The clinching pipe 4 is made of metal such as stainless steel and formed to be substantially cylindrical and have a cross-section of an approximate circle. An outer diameter of the clinching pipe 4 is configured to be slightly (for example, for 0.05-0.1 mm) smaller than an inner diameter of the flexible tube 1 so that the outer diameter of the clinching pipe 4 loosely fits the inner diameter of the flexible tube 1. As the clinching pipe 4 is attached to the operating wire 2, the clinching pipe 4 is deformed to be yielded toward the center of the diameter of the clinching pipe 4 by external force applied from two directions which are in substantially symmetry positions at an angle of 180 degrees from each other with respect to an axis of the clinching pipe 4 and expanded in directions perpendicular to the directions of the external force at expanded portions 4a.

Figure 2:
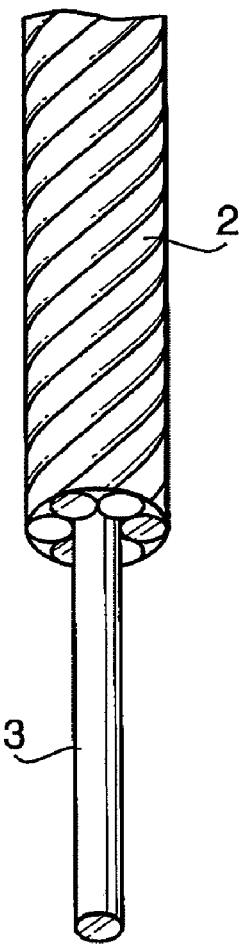
FIG. 2 is a perspective partial view of the high-frequency treatment tool for the endoscope without a clinching pipe according to the first embodiment of the invention.
Figure 3:
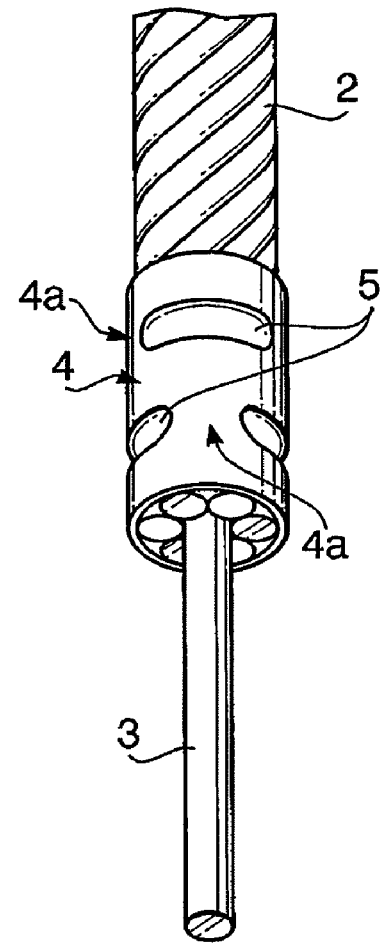
FIG. 3 is a perspective partial view of the high-frequency treatment tool for the endoscope with the clinching pipe attached according to the first embodiment of the invention.
Figure 4:
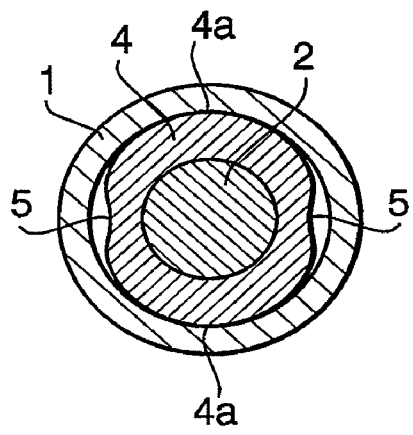
FIG. 4 is a cross-sectional view of the high-frequency treatment tool for the endoscope taken from IV-IV in FIG. 1 according to the first embodiment of the invention.
Figure 5:
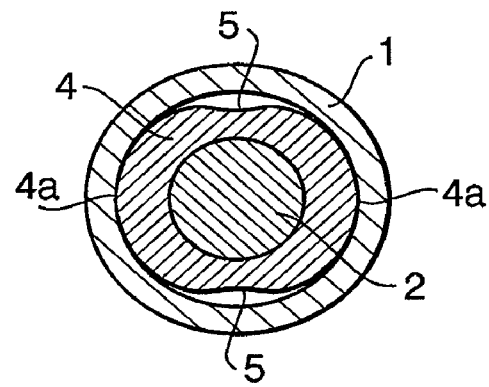
FIG. 5 is a cross-sectional view of the high-frequency treatment tool for the endoscope taken from V-V in FIG. 1 according to the first embodiment of the invention.

FIG. 2 is a perspective partial view of the high-frequency treatment tool 100 for the endoscope without the clinching pipe 4 according to the first embodiment of the invention. FIG. 3 is a perspective partial view of the high-frequency treatment tool 100 for the endoscope with the clinching pipe 4 attached according to the first embodiment of the invention. FIG. 4 is a cross-sectional view of the high-frequency treatment tool 100 for the endoscope taken from IV-IV in FIG. 1 according to the first embodiment of the invention. FIG. 5 is a cross-sectional view of the high-frequency treatment tool 100 for the endoscope taken from V-V in FIG. 1 according to the first embodiment of the invention. As shown in FIGS. 4 and 5, two sets of the clinching portions 5 are formed in axially displaced positions from each other with respect to the axis of the clinching pipe 4. Further, the two sets of the clinching portions 5 are in positions circumferentially separated at an angle of 90 degrees from each other on the circumference of the clinching pipe 4.

However, it should be noted that a number of sets of clinching portions 5 is not limited to two, but may be one, three, or more. If the number of sets of clinching portions 5 is three or more, the clinching portions 5 may be formed in axially evenly-spaced positions. Also, a number of clinching portions 5 provided in one set is not limited to two. Further, an angle between the clinching portions 5 in one set of clinching portions on the circumference of the clinching pipe 4 is not limited to 180 degrees. If the number of the clinching portions 5 in one set is three or more, the clinching portions 5 may be formed in circumferentially evenly-angled positions. Furthermore, an angle between the sets of clinching portions 5 to be axially displaced is not limited to 90 degrees.

With the above configuration, the clinching pipe 4 is halted stably on the operating wire 2. On the other hand, as the expanded portions 4a are in contact with the inner circumferential surface of the flexible tube 1, friction resistance is generated between the expanded portions 4a and the inner circumferential surface of the flexible tube 1.

Thus, the operating wire 2 can be arbitrarily advanced forward and retracted rearward and can be paused at an arbitrary position. Accordingly, the high-frequency electrode 3 arranged at the distal end of the operating wire 2 can be also protruded forward and retracted rearward from the distal end of the flexible tube 1 and can be paused at the arbitrary position. Therefore, the length of the high-frequency electrode 3 to be protruded from the distal end 1a of the flexible tube 1 can be arbitrarily adjusted without withdrawing the high-frequency treatment tool 100 itself from the forceps channel of the endoscope to attach a length adaptor so that mucous membranes and in vivo tissues can be incised with the preferable length of the high-frequency electrode 3 in the simple configuration and cost-effectively.

As shown in FIG. 1, the high-frequency treatment tool 100 is further provided with a cylindrical stopper 6, which is fixed to the distal end portion of the flexible tube 1. The stopper 6 may be pressedly and/or adhesively fixed to the flexible tube 1, but the method to fix the stopper 6 is not limited. For example, the stopper 6 may be provided with protrusions on an outer circumferential surface to wedge itself in the inner circumferential surface of the flexible tube 1. Further, the stopper 6 is formed to have a through hole 6a in a position corresponding to an axis of the stopper 6, and an inner diameter of the through hole 6a is substantially greater than the diameter of the high-frequency electrode 3 so that the high-frequency electrode 3 can penetrate therethrough.

With this configuration, a maximum length of the high-frequency electrode 3 to be protruded from the distal end 1a of the flexible tube 1 (i.e., a tip end side surface 6b of the stopper 6) is limited even if the operating wire 2 is forcibly advanced from the proximal end portion thereof, as the distal end of at least one of the operating wire 2 and the clinching pipe 4 becomes in contact with the stopper 6 and is stopped thereby.

Second Embodiment

Figure 7:
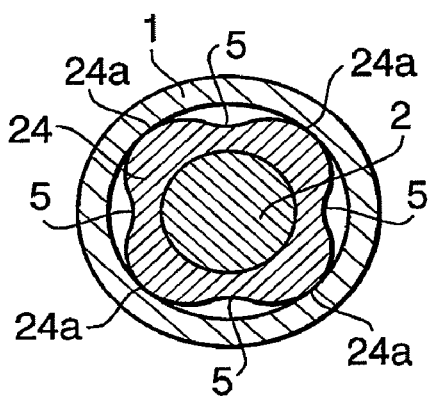
FIG. 7 is a cross-sectional view of the high-frequency treatment tool for the endoscope taken from VII-VII in FIG. 6 according to the second embodiment of the invention.
Figure 8:
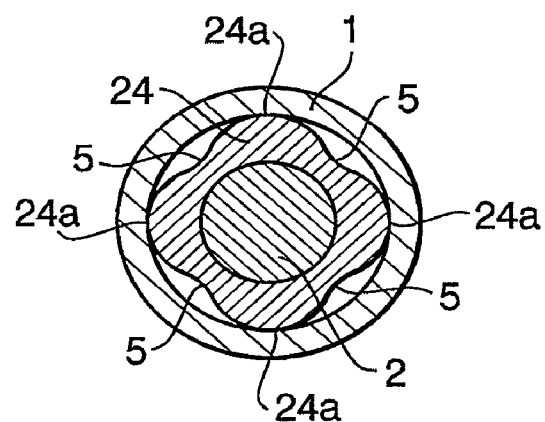
FIG. 8 is a cross-sectional view of the high-frequency treatment tool for the endoscope taken from VIII-VIII in FIG. 6 according to the second embodiment of the invention.
Figure 6:
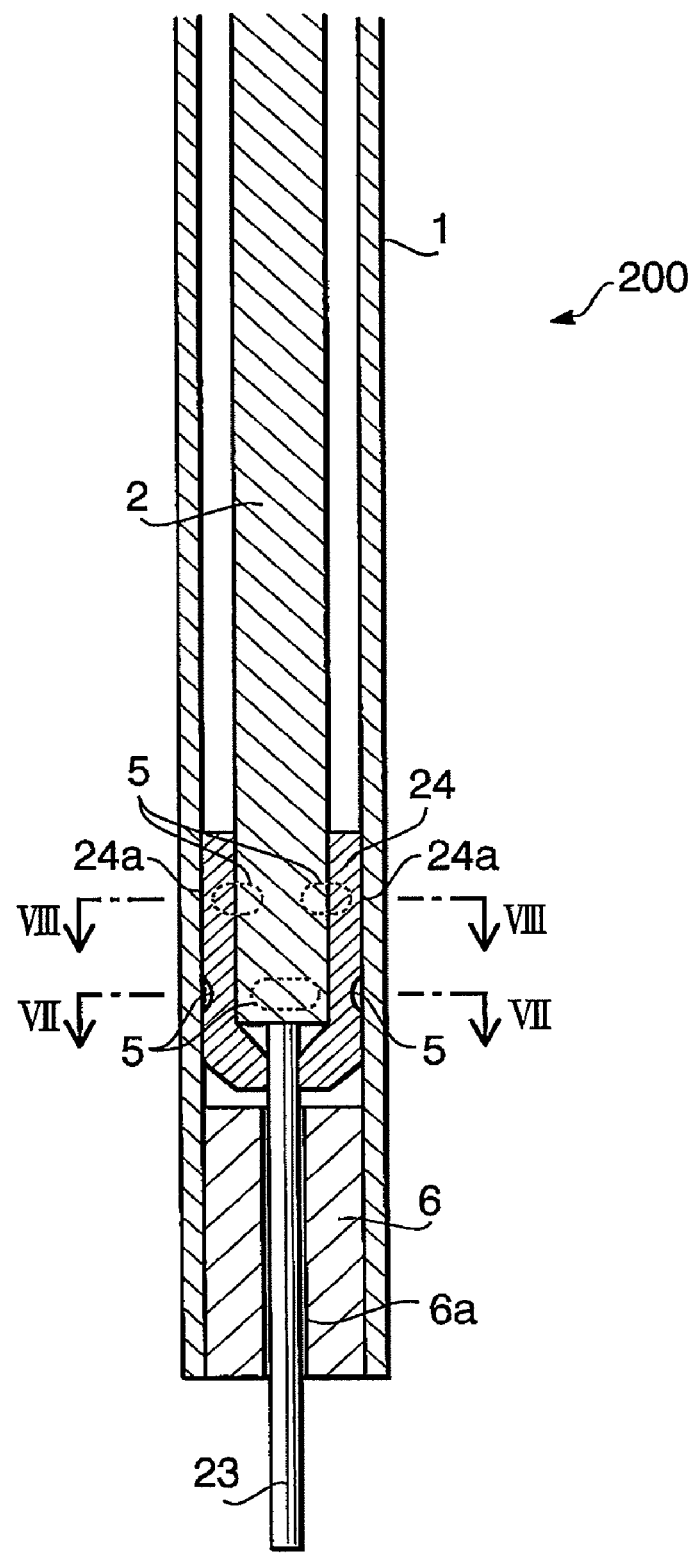
FIG. 6 is a cross-sectional side view of a distal end portion of a high-frequency treatment tool for an endoscope according to a second embodiment of the invention.

Referring now to FIGS. 6-8, a second embodiment of the present invention will be described. FIG. 6 is a cross-sectional side view of a distal end portion of a high-frequency treatment tool 200 for an endoscope according to a second embodiment of the invention. In the present and the following embodiments, a configuration similar to that of the first embodiment is referred to by an identical reference numeral, and description of that will be omitted. As shown in FIG. 6, the high-frequency treatment tool 200 is provided with a rod-like high-frequency electrode 23, which is fixed to the distal end of the operating wire 2 but formed independently from the operating wire 2. A base portion of the high-frequency electrode 23 is fixed to the distal end portion of the clinching pipe 24, and a base surface of the high-frequency electrode 23 is substantially flat against a distal plane of the operating wire 2. It should be noted that such a configuration of the high-frequency electrode 23 is preferable when the high-frequency electrode 23 is required to be larger in the diameter thereof.

In the present embodiment, the clinching pipe 24 is configured to halt the distal end portion of the operating wire 2 and formed to protrude forward (downward in FIG. 6) from the distal end of the operating wire 2 so that the high-frequency electrode 23 can be held thereby. In this configuration, the clinching pipe 24 serves to structurally and electrically connect the operating wire 2 and the high-frequency electrode 23.

FIG. 7 is a cross-sectional view of the high-frequency treatment tool 200 for the endoscope taken from VII-VII in FIG. 6 according to the second embodiment of the invention. FIG. 8 is a cross-sectional view of the high-frequency treatment tool 200 for the endoscope taken from VIII-VIII in FIG. 6 according to the second embodiment of the invention. It should be noted that, as shown in FIGS. 7 and 8, the clinching pipe 24 is formed to have two sets of clinching portions 5 on the circumferential surface thereof in axially displaced positions with respect to each other.

In the present embodiment, each of the sets of clinching portions 5 includes four clinching portions 5, which are formed in positions circumferentially separated at an angle of 90 degrees from one another on the circumference of the clinching pipe 24 with respect to the axis of the clinching pipe 24. Each of the sets of the clinching portions 5 is formed on the circumferential surface of the clinching pipe 24 in a position axially displaced at an angle of 45 degrees from each other. However, it should be noted that the number of sets of the clinching portions 5 is not limited to two, but may be three or more. When the number of sets of the clinching portions 5 is three or more, the sets of the clinching portions 5 may be formed in circumferentially evenly-angled positions.

With the above configuration, the operating wire 2 can be paused on the clinching pipe 24 more stably, and the friction resistance occurs evenly between the inner circumferential surface of the flexible tube 1 and the outer circumferential surface of the clinching pipe 4 so that the length of the high-frequency electrode 23 to be protruded from the distal end of the flexible tube 1 can be paused in an arbitrary position more stably.

It should be noted that in the present embodiment the configuration of the stopper 6 is similar to that of the stopper 6 in the first embodiment, however, as the distal surface of the clinching pipe 24 is protruded forward compared to the distal surface of the operating wire 2, the distal surface of the clinching pipe 4 is pressed against the stopper 6 as the maximum length of the high-frequency electrode 23 is restricted by the stopper 6.

Third Embodiment

Figure 9:
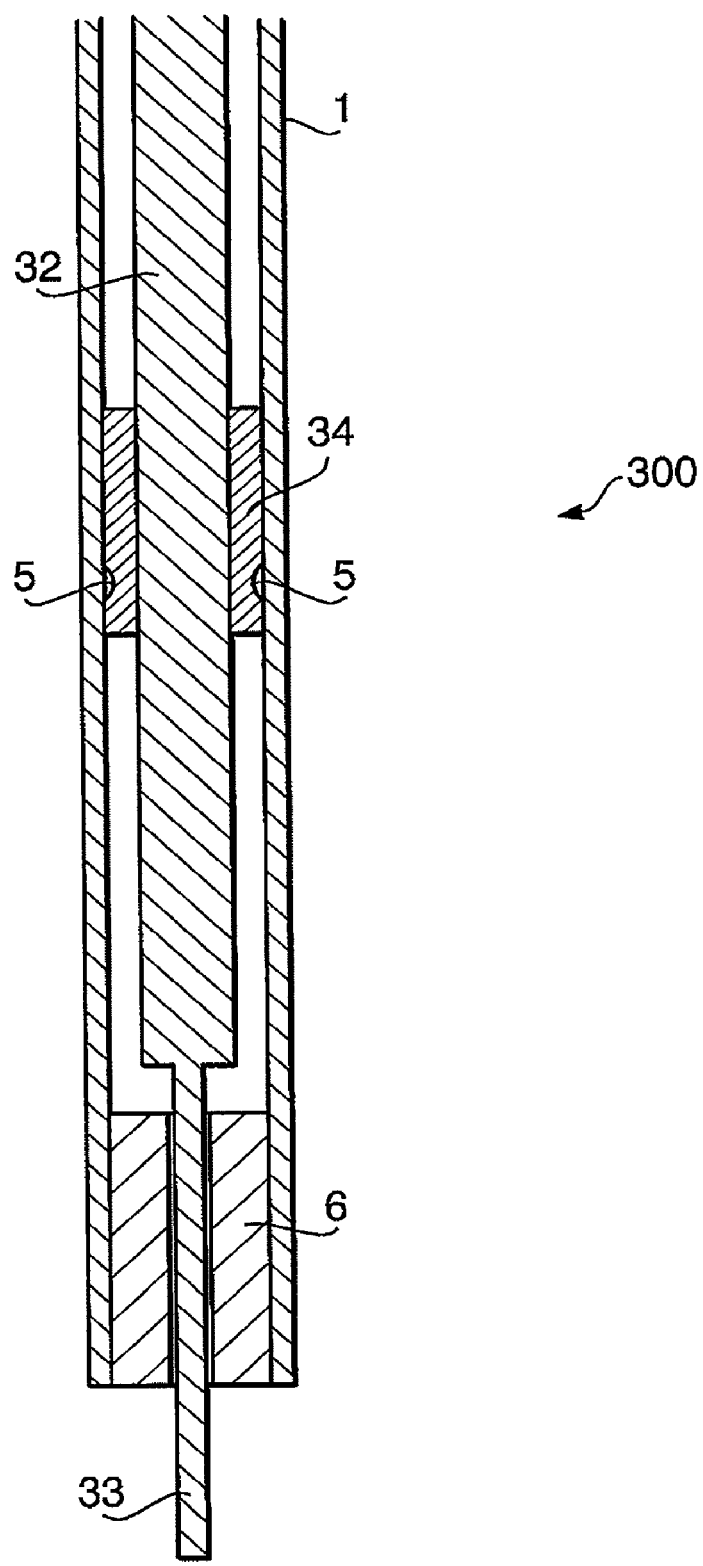
FIG. 9 is a cross-sectional side view of a distal end portion of a high-frequency treatment tool for an endoscope according to a third embodiment of the invention.

FIG. 9 is a cross-sectional side view of a distal end portion of a high-frequency treatment tool 300 for an endoscope according to a third embodiment of the invention. In the present embodiment, a high-frequency electrode 33 is configured with a core wire of the operating wire 32 with the strand wires removed therefrom, similarly to the high-frequency electrode 3 of the first embodiment.

However, it should be noted that a clinching pipe 34 in the present embodiment is attached to the operating wire 32 in a position shifted rearward toward the proximal end of the operating wire 32. In addition, the distal end portion of the operating wire 32 (excluding the high-frequency electrode 33) is bundled together for example by brazing or soldering so that the strand wires are prevented from being unwound. With this configuration, although manufacturing cost for the high-frequency treatment tool 300 may increase to a certain extent, the configuration and the functionality remain unaffected and substantially equivalent to the functionality of the high-frequency treatment tools 100, 200.

Fourth Embodiment

Figure 10:
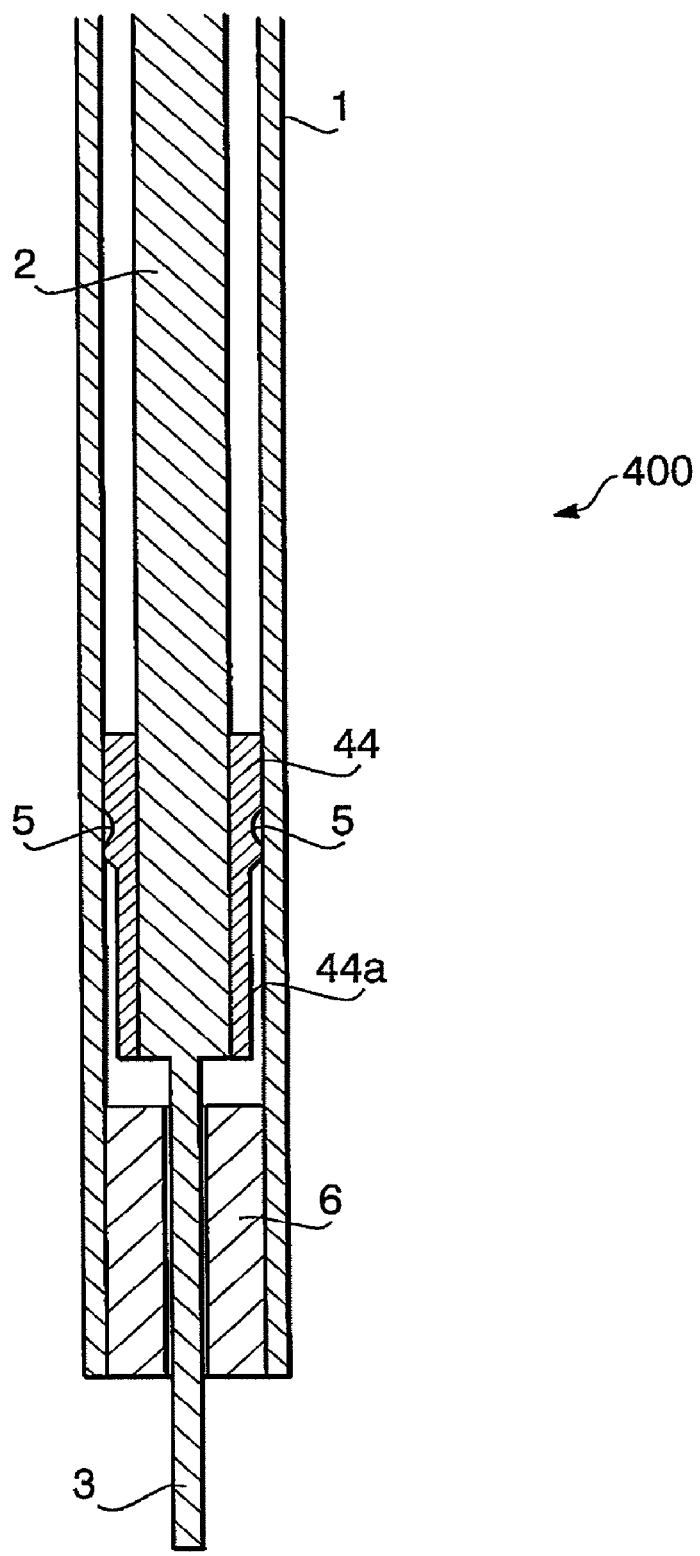
FIG. 10 is a cross-sectional side view of a distal end portion of a high-frequency treatment tool for an endoscope according to a fourth embodiment of the invention.

FIG. 10 is a cross-sectional side view of a distal end portion of a high-frequency treatment tool 400 for an endoscope according to a fourth embodiment of the invention. As shown in FIG. 10, the clinching pipe 44 is configured to have a smaller diameter than the inner diameter of the flexible tube 1 in a half portion thereof (in FIG. 10, a front half portion 44a), which is closer to the high-frequency electrode 3 in the axial direction. It should be noted that a rear half portion of the clinching pipe 44 instead of the front half portion may be configured to have the smaller diameter. With this configuration, the manufacturing cost and the functionality of the high-frequency treatment tool 400 remains unaffected and substantially equivalent to those of the high-frequency treatment tool 100.

Although examples of carrying out the invention have been described above, the present invention is not limited to the above described embodiments. For example, the clinching pipe 34 in the third embodiment may be attached to the rearward shifted position in the high-frequency treatment tools 100, 200, 400 of the above embodiments in addition to the clinching pipe 4, 24, and 44 respectively.

The present disclosure relates to the subject matter contained in Japanese Patent Application No. P2006-052689, filed on Feb. 28, 2006, which is expressly incorporated herein by reference in its entirety.

What is claimed is:

1. A high-frequency treatment tool for an endoscope, the high-frequency treatment tool comprising;
    an electrically insulating flexible tube insertable into an instrument channel of the endoscope;
    an operating wire comprising a core wire and a plurality of strand wires twisted around the core wire, wherein the operating wire is configured to be electrically conductive and movable inside the flexible tube in an axial direction of the flexible tube;
    the plurality of strand wires being removed from the operating wire at a distal end portion of the operating wire while a remaining portion of the core wire, at the distal end portion of the operating wire, defines a high-frequency electrode, wherein the high-frequency electrode is configured to be protrusible and retractable from a distal end of the flexible tube in the axial direction of the flexible tube according to movement of the operating wire; and
    a tubular member fitted on the distal end portion of the operating wire, the tubular member being plastically deformed and immovably attached onto the distal end portion of the operating wire in which the strand wires are maintained around the core wire, the deformation of the tubular member being caused as at least a part of the tubular member is deformed to interfere with an inner circumferential surface of the flexible tube so that the operating wire is halted with respect to the flexible tube at an arbitrary position in the flexible tube by frictional resistance caused between an interfering part of the tubular member and the inner circumferential surface of the flexible tube, and the high-frequency electrode to be protruded and retracted from the distal end of the flexible tube is halted in an arbitrary position.

2. The high-frequency treatment tool according to claim 1, wherein a cross-section of the inner circumferential surface of the flexible tube and a cross-section of an outer circumferential surface of the tubular member prior to the plastic deformation are substantially circular.

3. The high-frequency treatment tool according to claim 2, wherein the tubular member is plastically deformed inwardly toward an axis of the tubular member in a plurality of axially and circumferentially displaced positions with respect to the axis of the tubular member.

4. The high-frequency treatment tool according to claim 3, wherein the tubular member is plastically deformed inwardly in two axially and circumferentially displaced positions which are circumferentially separated at an angle of substantially 90 degrees from each other.

5. The high-frequency treatment tool according to claim 1, wherein the tubular member is plastically deformed inwardly toward an axis of the tubular member in a plurality of axially and circumferentially displaced positions with respect to the axis of the tubular member.

6. The high-frequency treatment tool according to claim 5, wherein the tubular member is plastically deformed inwardly in two axially and circumferentially displaced positions which are circumferentially separated at an angle of substantially 90 degrees from each other.

7. The high-frequency treatment tool according to claim 1, wherein the tubular member is plastically deformed inwardly toward the axis of the tubular member in four circumferentially displaced but axially coinciding positions which are circumferentially separated at an angle of substantially 90 degrees from one another.

8. The high-frequency treatment tool according to claim 1, wherein the tubular member is plastically deformed inwardly toward the axis of the tubular member in a set of four circumferentially displaced but axially coinciding positions which are circumferentially separated at an angle of substantially 90 degrees from each other;
    wherein the tubular member is plastically deformed inwardly toward the axis of the tubular member in another set of four circumferentially displaced but axially coinciding positions which are circumferentially separated at an angle of substantially 90 degrees from each other; and
    wherein the two sets of four circumferentially displaced but axially coinciding positions are axially displaced from each other and circumferentially separated at an angle of 45 degrees from each other.

9. The high-frequency treatment tool according to claim 1, comprising a stopper at a distal end portion thereof,
    wherein a length of the high-frequency electrode to be protruded from the distal end of the flexible tube is restricted when at least one of a distal end of the operating wire and a distal end of the tubular member becomes in contact with a proximal end portion of the stopper.

10. The high-frequency treatment tool according to claim 1,
    wherein the plurality of strand wires twisted around the core wire are bundled together by one of brazing and soldering at the distal end portion of the operating wire in which the strand wires are maintained around the core wire.

11. The high-frequency treatment tool according to claim 1,
    wherein the tubular member is formed to have a protruded portion, which protrudes further from a distal end portion of the operating wire toward the distal end of the flexible tube when the tubular member is immovably attached to the operating wire; and wherein a proximal end of the high-frequency electrode is attached to the distal end portion of the operating wire inside the protruded portion of the tubular member.

12. The high-frequency treatment tool according to claim 11, wherein the high-frequency electrode and the operating wire are electrically conducted via the tubular member.

13. The high-frequency treatment tool according to claim 1, wherein the tubular member is configured to have a smaller outer diameter portion, in which an outer diameter thereof is formed to be smaller than an outer diameter of the remaining portion of the tubular member.

14. The high-frequency treatment tool according to claim 1, wherein the high-frequency electrode is formed to have a shape of a straight rod.

* * * * *